(12) United States Patent
Domankevitz et al.

(10) Patent No.: US 11,813,474 B2
(45) Date of Patent: Nov. 14, 2023

(54) COSMETIC METHOD AND APPARATUS FOR SELECTING AN IPL LIGHT SOURCE HAVING A BAND PASS FILTER EQUIVALENT TO A SPECIFIED WAVELENGTH LASER LIGHT SOURCE FOR PROVIDING COSMETIC TREATMENT OF SKIN TISSUE

(71) Applicant: LUMENIS BE LTD., Yokneam (IL)

(72) Inventors: Yacov Domankevitz, Zichron Yaacov (IL); Israel Schuster, Kiryat-Tivon (IL)

(73) Assignee: LUMENIS BE LTD., Yokneam (IL)

( * ) Notice: Subject to any disclaimer, the term of this patent is extended or adjusted under 35 U.S.C. 154(b) by 0 days.

(21) Appl. No.: 17/836,160

(22) Filed: Jun. 9, 2022

(65) Prior Publication Data
US 2022/0305283 A1 Sep. 29, 2022

Related U.S. Application Data

(60) Division of application No. 16/221,545, filed on Dec. 16, 2018, now abandoned, which is a continuation of application No. PCT/US2017/038781, filed on Jun. 22, 2017.

(60) Provisional application No. 62/354,187, filed on Jun. 24, 2016.

(51) Int. Cl.
*A61N 5/06* (2006.01)
*A61B 18/20* (2006.01)
*A61B 18/00* (2006.01)

(52) U.S. Cl.
CPC .......... *A61N 5/0616* (2013.01); *A61B 18/203* (2013.01); *A61B 2018/00452* (2013.01); *A61B 2018/207* (2013.01); *A61N 2005/0662* (2013.01); *A61N 2005/0667* (2013.01)

(58) Field of Classification Search
None
See application file for complete search history.

(56) References Cited

U.S. PATENT DOCUMENTS

| | | |
|---|---|---|
| 5,885,273 A | 3/1999 | Eckhouse et al. |
| 7,094,252 B2 | 8/2006 | Koop |
| 2003/0069567 A1* | 4/2003 | Eckhouse ............ A61B 18/203 606/9 |
| 2004/0147986 A1 | 7/2004 | Baumgardner et al. |
| 2007/0088408 A1* | 4/2007 | Amornsiripanitch ...... A61B 18/203 607/101 |
| 2007/0191821 A1 | 8/2007 | Boxer Wachler et al. |
| 2008/0200908 A1 | 8/2008 | Domankevitz |
| 2010/0131035 A1 | 5/2010 | Hamada et al. |

(Continued)

OTHER PUBLICATIONS

Goldberg DJ. Current trends in intense pulsed light. J Clin Aesthet Dermatol. Jun. 2012;5(6):45-53. PMID: 22768357; PMCID: PMC3390232 (Year: 2012).*

(Continued)

*Primary Examiner* — Ankit D Tejani
(74) *Attorney, Agent, or Firm* — ISUS INTELLECTUAL PROPERTY PLLC; Anthony Jason Mirabito

(57) ABSTRACT

A cosmetic method and apparatus for selecting an IPL light source having a band pass filter equivalent to a specified wavelength laser light source for providing cosmetic treatment of skin tissue and being configured to deliver high energy fluences and achieve a threshold energy sufficient to produce a clinical effect during operation.

7 Claims, 14 Drawing Sheets

(56) References Cited

U.S. PATENT DOCUMENTS

2015/0057701 A1 2/2015 Kelleher et al.
2016/0374173 A1 12/2016 Vidal .................. A61N 5/0616

OTHER PUBLICATIONS

Husain Z, Alster TS. The role of lasers and intense pulsed light technology in dermatology. Clin Cosmet Investig Dermatol. 2016;9: 29-40. Published Feb. 4, 2016. doi:10.2147/CCID.S69106 (Year: 2016).*

* cited by examiner

| BLOOD | |
|---|---|
| LASER WAVELENGTH (nm) | ABSORPTION COEFF.($cm^{-1}$) |
| 532 | 232 |
| 577 | 262 |
| 585 | 170 |
| 595 | 60 |
| 940 | 6 |
| 1064 | 2 |

FIG.2

| MELANIN | |
|---|---|
| LASER WAVELENGTH (nm) | ABSORPTION COEFF.(cm$^{-1}$) |
| 532 | 550 |
| 595 | 381 |
| 694 | 227 |
| 755 | 172 |
| 1064 | 55 |

|  | Alexandrite like | | |
|---|---|---|---|
|  | Band pass filter: |  | 675-900 |
|  | Averaged absorption coefficient: |  | 165.26 |
|  |  |  |  |
|  |  |  |  |
| Wavelength | Blood | Melanin | Melanin/blood Ratio |
|  |  |  |  |
| 455 | 248.9291801 | 929.7495668 | 3.734996301 |
| 460 | 206.0261835 | 896.5207712 | 4.351489485 |
| 465 | 175.597186 | 864.8197566 | 4.925020591 |
| 470 | 151.7129879 | 834.560967 | 5.500919722 |
| 475 | 135.6047892 | 805.6644773 | 5.941268611 |
| 480 | 124.2323901 | 778.0555681 | 6.262904286 |
| 485 | 119.1239905 | 751.6643379 | 6.309932491 |
| 490 | 116.5319907 | 726.4253462 | 6.233698935 |
| 495 | 113.9588909 | 702.2772876 | 6.162549338 |
| 500 | 112.908591 | 679.162692 | 6.015155147 |
| 505 | 114.0209909 | 657.0276498 | 5.762339414 |
| 510 | 117.4985906 | 635.8215583 | 5.411312213 |
| 515 | 124.76429 | 615.49689 | 4.933277702 |
| 520 | 142.6517886 | 596.0089772 | 4.17806873 |
| 525 | 173.7206861 | 577.3158156 | 3.323241628 |
| 530 | 214.2935829 | 559.3778814 | 2.610334262 |
| 535 | 252.1070798 | 542.1579636 | 2.150506697 |
| 540 | 276.7229779 | 525.6210087 | 1.899448368 |
| 545 | 274.517078 | 509.7339769 | 1.856838855 |
| 550 | 249.1397801 | 494.4657098 | 1.984691925 |
| 555 | 223.0955822 | 479.786807 | 2.150588561 |
| 560 | 210.4055832 | 465.6695126 | 2.21319941 |
| 565 | 213.6077829 | 452.0876094 | 2.116437909 |
| 570 | 241.2233807 | 439.0163212 | 1.819957584 |

FIG.8

| | | | |
|---|---|---|---|
| 575 | 271.9925782 | 426.4322214 | 1.567808299 |
| 580 | 249.3503801 | 414.3131493 | 1.661570154 |
| 585 | 170.1593864 | 402.638131 | 2.366241085 |
| 590 | 100.310392 | 391.3873068 | 3.901762311 |
| 595 | 59.57576523 | 380.5418627 | 6.387527902 |
| 600 | 35.87759713 | 370.0839679 | 10.31518266 |
| 605 | 26.90792785 | 359.9967151 | 13.37883456 |
| 610 | 20.99195832 | 350.2640661 | 16.68563079 |
| 615 | 16.64603867 | 340.8708001 | 20.47759271 |
| 620 | 14.10695887 | 331.8024661 | 23.52048156 |
| 625 | 12.13709303 | 323.0453379 | 26.61636828 |
| 630 | 10.64717915 | 314.5863727 | 29.54645248 |
| 635 | 9.433097245 | 306.4131717 | 32.48277461 |
| 640 | 8.709659303 | 298.5139438 | 34.27389447 |
| 645 | 8.026235358 | 290.8774711 | 36.24083498 |
| 650 | 7.466039403 | 283.4930771 | 37.97101272 |
| 655 | 6.926363446 | 276.3505966 | 39.89836785 |
| 660 | 6.435827485 | 269.4403477 | 41.86568833 |
| 665 | 6.032987517 | 262.7531049 | 43.55273472 |
| 670 | 5.639219549 | 256.2800751 | 45.44601835 |
| 675 | 5.270183578 | 250.0128737 | 47.43912048 |
| 680 | 4.950287604 | 243.9435032 | 49.27865261 |
| 685 | 4.637897629 | 238.0643322 | 51.33022573 |
| 690 | 4.367519651 | 232.3680767 | 53.20367057 |
| 695 | 4.176737666 | 226.8477814 | 54.31219282 |
| 700 | 4.00247968 | 221.4968031 | 55.33989446 |
| 705 | 3.826331694 | 216.308794 | 56.5316369 |
| 710 | 3.681719705 | 211.2776873 | 57.38559809 |
| 715 | 3.562757715 | 206.3976824 | 57.93200069 |
| 720 | 3.463559723 | 201.6632316 | 58.2242686 |

FIG.8 (cont. 1)

| | | | |
|---|---|---|---|
| 725 | 3.37467573 | 197.0690276 | 58.39643372 |
| 730 | 3.259439739 | 192.6099912 | 59.09297505 |
| 735 | 3.347135732 | 188.2812602 | 56.25145654 |
| 740 | 3.49379972 | 184.0781788 | 52.687101 |
| 745 | 3.819041694 | 179.9962873 | 47.13127055 |
| 750 | 4.234139661 | 176.031313 | 41.57428123 |
| 755 | 4.611275631 | 172.1791608 | 37.33872675 |
| 760 | 4.724459622 | 168.4359046 | 35.65188785 |
| 765 | 4.655501628 | 164.7977798 | 35.39850117 |
| 770 | 4.582439633 | 161.2611753 | 35.19111831 |
| 775 | 4.507865639 | 157.8226263 | 35.01049919 |
| 780 | 4.425299646 | 154.4788076 | 34.90810114 |
| 785 | 4.362616451 | 151.226527 | 34.66418117 |
| 790 | 4.300759456 | 148.0627194 | 34.42711012 |
| 795 | 4.267117459 | 144.9844406 | 33.97713842 |
| 800 | 4.318433655 | 141.9888621 | 32.87971369 |
| 805 | 4.363793651 | 139.0732661 | 31.86980806 |
| 810 | 4.427621646 | 136.2350397 | 30.76934992 |
| 815 | 4.480406642 | 133.4716712 | 29.79007977 |
| 820 | 4.586419433 | 130.780745 | 28.51478085 |
| 825 | 4.716559423 | 128.1599375 | 27.17233602 |
| 830 | 4.804379616 | 125.607013 | 26.14427315 |
| 835 | 4.888187609 | 123.1198201 | 25.18721251 |
| 840 | 4.984831401 | 120.6962878 | 24.21271215 |
| 845 | 5.076631394 | 118.3344222 | 23.30963449 |
| 850 | 5.11912939 | 116.0323032 | 22.66641344 |
| 855 | 5.161724587 | 113.7880811 | 22.0445859 |
| 860 | 5.25250938 | 111.5999739 | 21.24698231 |
| 865 | 5.345108572 | 109.4662644 | 20.4797083 |
| 870 | 5.407219367 | 107.3852974 | 19.85961547 |

FIG.8 (cont. 2)

| | | | |
|---|---|---|---|
| 875 | 5.471252562 | 105.3554773 | 19.25618971 |
| 880 | 5.538871357 | 103.3752653 | 18.66359745 |
| 885 | 5.603687552 | 101.4431775 | 18.1029325 |
| 890 | 5.657471547 | 99.55778219 | 17.59757541 |
| 895 | 5.710013543 | 97.71769811 | 17.11339165 |
| 900 | 5.762539339 | 95.92159223 | 16.64571582 |
| 905 | 5.809465335 | 94.16817782 | 16.20943966 |
| 910 | 5.843771532 | 92.45621264 | 15.82132568 |
| 915 | 5.87228353 | 90.78449713 | 15.45982865 |
| 920 | 5.886091329 | 89.15187274 | 15.14619257 |
| 925 | 5.892749529 | 87.55722031 | 14.8584663 |
| 930 | 5.856499331 | 85.99945853 | 14.68444777 |
| 935 | 5.781374537 | 84.47754247 | 14.6120169 |
| 940 | 5.712211343 | 82.99046215 | 14.52860498 |
| 945 | 5.631859349 | 81.53724122 | 14.47785468 |
| 950 | 5.526683558 | 80.11693567 | 14.49638555 |
| 955 | 5.430833566 | 78.72863255 | 14.49660197 |
| 960 | 5.334551573 | 77.37144886 | 14.50383369 |
| 965 | 5.228036582 | 76.04453036 | 14.54552377 |
| 970 | 5.087825593 | 74.74705054 | 14.69135472 |
| 975 | 4.978745602 | 73.47820955 | 14.758378 |
| 980 | 4.846537412 | 72.2372332 | 14.90491604 |
| 985 | 4.705208624 | 71.02337206 | 15.09462762 |
| 990 | 4.541167437 | 69.8359005 | 15.37840246 |
| 995 | 4.37354065 | 68.67411583 | 15.70217847 |
| 1000 | 4.205735664 | 67.53733749 | 16.05838857 |

FIG.8 (cont. 3)

| | KTP like | | |
|---|---|---|---|
| | Band pass filter: | | 525-585 |
| | Averaged absorption coefficient: | | 232.3335 |
| | | | |
| Wavelength | Blood | Melanin | Melanin/blood Ratio |
| 455 | 248.9291801 | 929.7495668 | 3.7349963 |
| 460 | 206.0261835 | 896.5207712 | 4.3514895 |
| 465 | 175.597186 | 864.8197566 | 4.9250206 |
| 470 | 151.7129879 | 834.560967 | 5.5009197 |
| 475 | 135.6047892 | 805.6644773 | 5.9412686 |
| 480 | 124.2323901 | 778.0555681 | 6.2629043 |
| 485 | 119.1239905 | 751.6643379 | 6.3099325 |
| 490 | 116.5319907 | 726.4253462 | 6.2336989 |
| 495 | 113.9588909 | 702.2772876 | 6.1625493 |
| 500 | 112.908591 | 679.162692 | 6.0151551 |
| 505 | 114.0209909 | 657.0276498 | 5.7623394 |
| 510 | 117.4985906 | 635.8215583 | 5.4113122 |
| 515 | 124.76429 | 615.49689 | 4.9332777 |
| 520 | 142.6517886 | 596.0089772 | 4.1780687 |
| 525 | 173.7206861 | 577.3158156 | 3.3232416 |
| 530 | 214.2935829 | 559.3778814 | 2.6103343 |
| 535 | 252.1070798 | 542.1579636 | 2.1505067 |
| 540 | 276.7229779 | 525.6210087 | 1.8994484 |
| 545 | 274.517078 | 509.7339769 | 1.8568389 |
| 550 | 249.1397801 | 494.4657098 | 1.9846919 |

FIG.9

| | | | | | |
|---|---|---|---|---|---|
| 555 | 223.0955822 | 479.786807 | 2.1505886 | | |
| 560 | 210.4055832 | 465.6695126 | 2.2131994 | | |
| 565 | 213.6077829 | 452.0876094 | 2.1164379 | | |
| 570 | 241.2233807 | 439.0163212 | 1.8199576 | | |
| 575 | 271.9925782 | 426.4322214 | 1.5678083 | | |
| 580 | 249.3503801 | 414.3131493 | 1.6615702 | | |
| 585 | 170.1593864 | 402.638131 | 2.3662411 | | |
| 590 | 100.310392 | 391.3873068 | 3.9017623 | | |
| 595 | 59.57576523 | 380.5418627 | 6.3875279 | | |
| 600 | 35.87759713 | 370.0839679 | 10.315183 | | |
| 605 | 26.90792785 | 359.9967151 | 13.378835 | | |
| 610 | 20.99195832 | 350.2640661 | 16.685631 | | |
| 615 | 16.64603867 | 340.8708001 | 20.477593 | | |
| 620 | 14.10695887 | 331.8024661 | 23.520482 | | |
| 625 | 12.13709303 | 323.0453379 | 26.616368 | | |
| 630 | 10.64717915 | 314.5863727 | 29.546452 | | |
| 635 | 9.433097245 | 306.4131717 | 32.482775 | | |
| 640 | 8.709659303 | 298.5139438 | 34.273894 | | |
| 645 | 8.026235358 | 290.8774711 | 36.240835 | | |
| 650 | 7.466039403 | 283.4930771 | 37.971013 | | |
| 655 | 6.926363446 | 276.3505966 | 39.898368 | | |
| 660 | 6.435827485 | 269.4403477 | 41.865688 | | |
| 665 | 6.032987517 | 262.7531049 | 43.552735 | | |
| 670 | 5.639219549 | 256.2800751 | 45.446018 | | |
| 675 | 5.270183578 | 250.0128737 | 47.43912 | | |
| 680 | 4.950287604 | 243.9435032 | 49.278653 | | |
| 685 | 4.637897629 | 238.0643322 | 51.330226 | | |
| 690 | 4.367519651 | 232.3680767 | 53.203671 | | |
| 695 | 4.176737666 | 226.8477814 | 54.312193 | | |
| 700 | 4.00247968 | 221.4968031 | 55.339894 | | |

FIG.9 (cont. 1)

| | | | | | |
|---|---|---|---|---|---|
| | 705 | 3.826331694 | 216.308794 | 56.531637 | |
| | 710 | 3.681719705 | 211.2776873 | 57.385598 | |
| | 715 | 3.562757715 | 206.3976824 | 57.932001 | |
| | 720 | 3.463559723 | 201.6632316 | 58.224269 | |
| | 725 | 3.37467573 | 197.0690276 | 58.396434 | |
| | 730 | 3.259439739 | 192.6099912 | 59.092975 | |
| | 735 | 3.347135732 | 188.2812602 | 56.251457 | |
| | 740 | 3.49379972 | 184.0781788 | 52.687101 | |
| | 745 | 3.819041694 | 179.9962873 | 47.131271 | |
| | 750 | 4.234139661 | 176.031313 | 41.574281 | |
| | 755 | 4.611275631 | 172.1791608 | 37.338727 | |
| | 760 | 4.724459622 | 168.4359046 | 35.651888 | |
| | 765 | 4.655501628 | 164.7977798 | 35.398501 | |
| | 770 | 4.582439633 | 161.2611753 | 35.191118 | |
| | 775 | 4.507865639 | 157.8226263 | 35.010499 | |
| | 780 | 4.425299646 | 154.4788076 | 34.908101 | |
| | 785 | 4.362616451 | 151.226527 | 34.664181 | |
| | 790 | 4.300759456 | 148.0627194 | 34.42711 | |
| | 795 | 4.267117459 | 144.9844406 | 33.977138 | |
| | 800 | 4.318433655 | 141.9888621 | 32.879714 | |
| | 805 | 4.363793651 | 139.0732661 | 31.869808 | |
| | 810 | 4.427621646 | 136.2350397 | 30.76935 | |
| | 815 | 4.480406642 | 133.4716712 | 29.79008 | |
| | 820 | 4.586419433 | 130.780745 | 28.514781 | |
| | 825 | 4.716559423 | 128.1599375 | 27.172336 | |
| | 830 | 4.804379616 | 125.607013 | 26.144273 | |
| | 835 | 4.888187609 | 123.1198201 | 25.187213 | |
| | 840 | 4.984831401 | 120.6962878 | 24.212712 | |
| | 845 | 5.076631394 | 118.3344222 | 23.309634 | |
| | 850 | 5.11912939 | 116.0323032 | 22.666413 | |

FIG.9 (cont. 2)

| | | | | |
|---:|---:|---:|---:|---|
| 855 | 5.161724587 | 113.7880811 | 22.044586 | |
| 860 | 5.25250938 | 111.5999739 | 21.246982 | |
| 865 | 5.345108572 | 109.4662644 | 20.479708 | |
| 870 | 5.407219367 | 107.3852974 | 19.859615 | |
| 875 | 5.471252562 | 105.3554773 | 19.25619 | |
| 880 | 5.538871357 | 103.3752653 | 18.663597 | |
| 885 | 5.603687552 | 101.4431775 | 18.102932 | |
| 890 | 5.657471547 | 99.55778219 | 17.597575 | |
| 895 | 5.710013543 | 97.71769811 | 17.113392 | |
| 900 | 5.762539339 | 95.92159223 | 16.645716 | |
| 905 | 5.809465335 | 94.16817782 | 16.20944 | |
| 910 | 5.843771532 | 92.45621264 | 15.821326 | |
| 915 | 5.87228353 | 90.78449713 | 15.459829 | |
| 920 | 5.886091329 | 89.15187274 | 15.146193 | |
| 925 | 5.892749529 | 87.55722031 | 14.858466 | |
| 930 | 5.856499331 | 85.99945853 | 14.684448 | |
| 935 | 5.781374537 | 84.47754247 | 14.612017 | |
| 940 | 5.712211343 | 82.99046215 | 14.528605 | |
| 945 | 5.631859349 | 81.53724122 | 14.477855 | |
| 950 | 5.526683558 | 80.11693567 | 14.496386 | |
| 955 | 5.430833566 | 78.72863255 | 14.496602 | |
| 960 | 5.334551573 | 77.37144886 | 14.503834 | |
| 965 | 5.228036582 | 76.04453036 | 14.545524 | |
| 970 | 5.087825593 | 74.74705054 | 14.691355 | |
| 975 | 4.978745602 | 73.47820955 | 14.758378 | |
| 980 | 4.846537412 | 72.2372332 | 14.904916 | |
| 985 | 4.705208624 | 71.02337206 | 15.094628 | |
| 990 | 4.541167437 | 69.8359005 | 15.378402 | |
| 995 | 4.37354065 | 68.67411583 | 15.702178 | |
| 1000 | 4.205735664 | 67.53733749 | 16.058389 | |

FIG.9 (cont. 3)

COSMETIC METHOD AND APPARATUS FOR SELECTING AN IPL LIGHT SOURCE HAVING A BAND PASS FILTER EQUIVALENT TO A SPECIFIED WAVELENGTH LASER LIGHT SOURCE FOR PROVIDING COSMETIC TREATMENT OF SKIN TISSUE

RELATED APPLICATIONS

This application is a divisional application of U.S. application Ser. No. 16/221,545, filed Dec. 16, 2018, which is a continuation application of PCT/US2017/38781, filed Jun. 22, 2017, which claims the benefit of U.S. Provisional Application No. 62/354,187, filed Jun. 24, 2016, the entire contents of which are incorporated herein by reference.

FIELD OF THE INVENTION

The present invention relates to light treatments applied to human skin tissue and in particular to light treatments utilizing selective band pass filters in Intense Pulsed Light devices.

BACKGROUND

Optical energy radiation is a known modality for the treatment of skin disorders. In order to obtain a clinical effect in the skin, the irradiated optical energy will preferably be absorbed in the skin.

Light absorbance in the skin is dominated by three endogenous chromophores: water, melanin and hemoglobin. A correct matching between a light wavelength or a spectrum of wavelengths, with a targeted chromophore, may lead to an optical energy absorbance which may be followed by a clinical effect due to one or more of photothermal, photochemical or photomechanical effects. Light scattering effects, when light energy impinges on the skin, may affect the depth of light penetration into the tissue. Such effects, if any, are more dominant in the dermis than in the epidermis due to a higher concentration of collagen fibers in the dermis. In general, up to the mid-infrared region of light energy, the amount of scattering is inversely proportional to the wavelength of light. As mentioned by Anderson and Parrish, "Selective photothermolysis: precise microsurgery by selective absorption of pulsed radiation", Science, 1983 Apr. 29; 220(4596):524-7, selective laser treatment may be achieved by selecting the right wavelength to the right chromophore as mentioned above, by applying an energy pulse which is shorter or equal to the thermal relaxation time of the target chromophore and by delivering above-threshold energy to the target tissue. Different varieties of lasers and intense pulsed light (IPL) devices use these principles to deliver a wide range of optical treatments for skin disorders.

IPL devices emit polychromatic, non-coherent and non-collimated light in a spectrum range from about 400 nm to about 1,400 nm, and are normally delivered in a variety of pulse durations. As used herein, the term "about" may be taken to mean a variation of as much as +/−10 percent. IPL is less selective since different chromophores may be targeted in this range. One option to improve selectivity of IPL-generated light energy is by using filters. Cut off filters are used on the lower end of the emission spectrum of IPL devices and cut on filters are used on the upper end of the emission spectrum. Such filters may improve treatment selectivity or reduce parasitic wavelengths which may put the patient at risk, such as ultra-violet or increased bulk heating such as is possible with the presence of an infrared component in the light emitted. Common medical IPL cut off filters include 550, 560, 570, 590, 615, 645, 695, 755 and 780 nm filters. Cut off and cut on filters may be used together to create what is termed a band pass filter.

Band pass filters provided by some providers, such as Alma Lasers, for example, provide a narrow spectrum IPL based treatment within the range of 500 nm-600 nm for the treatment of vascular lesions which are targeted at larger blood vessels. An alternative narrow band pass filter is provided in the range of 550 nm-600 nm for skin rejuvenation. One of the problems with such filters is that, in the filtering process, they also remove part of the total optical energy produced by the light source, which is an IPL light source. Therefore, in order to produce a clinical effect by meeting the threshold-energy requirement mentioned above, only a limited amount of the spectrum can be removed.

In the laser domain, vascular lesions are treated by targeting intravascular chromophore of oxyhemoglobin which has light absorption peaks at 418 nm, 542 nm and 577 nm. The most common vascular lasers are KTP, 532 nm, pulsed dye laser (PDL) 585 nm-595 nm, Alexandrite 755 nm, diode laser 940-980 nm and Nd:YAG 532 or 1,064 nm. The PDL is considered the "workhorse" vascular laser.

An IPL light source may also be used for the treatment of vascular lesions, as mentioned above, using filters which include at least one of these absorption peaks and remove damaging UV wavelengths and/or infrared wavelengths which may cause collateral thermal damage. Two companies, Lumenis and Palomar, provide such dual band filters. For example, in the vascular dual band filter, the shorter wavelengths are used for smaller superficial vessels and the longer wavelengths are used for larger deeper vessels.

Pigmented lesions are also treated by lasers by targeting melanin in melanosomes as the target chromophore with lasers such as KTP (532 nm), Ruby (694 nm), alexandrite (755 nm), etc. using a variety of pulse durations ranging from milliseconds down to picoseconds. IPL may also be used for some pigmented lesions such as dyschromia or solar lentigines. Again, by selecting filters which generate the appropriate spectrum of optical energy provided that the spectrum is wide enough such that a sufficient amount of fluence reaches the target tissue, an IPL-powered device may be used to treat at least some pigmented lesions. However, the wider the spectrum, different chromophores may be targeted and selectivity may be decreased. Moreover, in order to avoid side effects of scarring or depigmentation, short pulses may be required to confine the area or volume of any thermal effects in the target tissue. These short pulses may be in the range of nanoseconds or less while IPL offers pulses in the range of milliseconds only.

The flexibility of using a single light source, IPL, in a device to treat various types of skin disorders at various types of skin remains very attractive. Therefore, there is a need for a more advanced system to provide an IPL-based treatment with a higher effective selectivity or a higher absorbance that is similar to the equivalent known laser wavelengths it is designed to mimic.

SUMMARY OF THE PRESENT INVENTION

In an aspect, a device for the cosmetic treatment of vascular lesions on skin tissue which is an equivalent of a laser with an operating wavelength of 532 nm, includes: an intense pulsed light (IPL) source, the IPL source being activatable; it further includes a band pass filter which blocks substantially all but one range of wavelengths of light emanating from the IPL source when activated; the band pass filter permits transmission of light from the IPL source when activated in the range of about 525 nm to about 585 nm; the IPL with the band pass filter provides equivalent cosmetic treatment as a laser with an operating wavelength of 532 nm.

In another aspect, a method of providing cosmetic treatment equivalent to a 532 nm laser on a body vascular region includes: providing an intense pulsed light (IPL) source; interposing a band pass filter between the IPL source and the body vascular region; the band pass filter is of a type that substantially passes light in the range of about 525 nm to about 585 nm; the method further includes activating the IPL source; the filtered light impinging on the vascular body portion provides cosmetic treatment equivalent to that of the 532 nm laser.

In yet another aspect, a cosmetic method of providing light treatment to skin tissue includes providing an intense pulsed light (IPL) source; interposing a band pass filter between the IPL source and the body vascular region; the band pass filter passes light in the range of about 525 nm to about 585 nm; the method further includes activating the IPL source and applying it to the skin tissue, wherein the filtered light impinging on the skin tissue provides equivalent treatment to that of a 532 nm laser.

In a further aspect, a band pass filter is the equivalent to a 532 nm laser impinging on skin tissue; the band pass filter is constructed to pass light through the filter substantially in the 525 nm to 585 nm range.

In yet a further aspect, a cosmetic method of providing light treatment to skin tissue includes the steps of providing an intense pulsed light (IPL) source; interposing a band pass filter between the IPL source and the skin tissue; the band pass filter passes light in a selected range of wavelengths with an average absorption coefficient equivalent to that of a selected laser light source; the method further includes activating the IPL source and applying it to the skin tissue, wherein the filtered light impinging on the skin tissue provides equivalent treatment to that of the selected laser light source.

In another aspect, a cosmetic method of providing an intense pulsed light (IPL) source equivalent in treatment effect to a selected laser light source includes for the selected laser light source of a specific wavelength, determining the average absorption coefficient of the specific wavelength in skin tissue; and, selecting a band pass filter with a substantially equivalent average absorption coefficient in skin tissue. The skin tissue may be one or more of: absorption in blood and absorption in melanin.

In a further aspect, the IPL source further includes a body portion which includes the IPL source and an opening in the body portion to accept one or more band pass filters and wherein the one or more band pass filters are filters which pass different ranges of light from the IPL source to the skin tissue. The one or more band pass filters may be in one or more of the following ranges: 560-690 nm; 675-900 nm; 700-800 nm; 725-775 nm; 940-980 nm.

In an aspect, a method of selecting an IPL light source having a band pass filter equivalent to a specified wavelength laser light source for providing cosmetic treatment of skin tissue includes the steps of: selecting a laser light source of a specified wavelength; activating the laser light source; directing the laser light source at a target; measuring the average absorption coefficient of the selected laser in the target; storing the measured coefficient; selecting a band pass filter; activating the IPL light source; measuring the average absorption coefficient of the selected band pass filter in the target; comparing the measured coefficient of the band pass filter with the stored measured coefficient of the selected laser light source; if the measured coefficients substantially match, determining that the selected laser light source and the IPL light source with the selected band pass filter are equivalent. The target may be skin tissue.

In an aspect, a method of selecting an IPL light source having a band pass filter equivalent to a specified wavelength laser light source for providing cosmetic treatment of skin tissue, includes the steps of: selecting a laser light source of a specified wavelength; activating the laser light source; directing the laser light source at a target; measuring the average depth of penetration of the selected laser in the target; storing the depth of penetration; selecting a band pass filter; activating the IPL light source; measuring the average depth of penetration of the selected band pass filter in the target; comparing the measured average penetration of the band pass filter with the stored measured average penetration of the selected laser light source; if the measured average depths of penetration substantially match, determining that the selected laser light source and the IPL light source with the selected band pass filter are equivalent.

In an aspect, a band pass filter is an equivalent to a 595 nm laser impinging on skin tissue; the band pass filter is constructed to pass light through the filter substantially in the 560 nm to 690 nm range. The light may be an IPL light source.

In an aspect, a band pass filter is an equivalent to a 755 nm laser impinging on skin tissue; the band pass filter is constructed to pass light through the filter substantially in the 700 nm to 800 nm range. The light may be an IPL light source.

In another aspect, a device for the cosmetic treatment of vascular lesions on skin tissue, wherein the device is an equivalent of a laser having an operating wavelength of 595 nm, includes an intense pulsed light (IPL) source, the IPL source being activatable; a band pass filter which blocks substantially all but one range of wavelengths of light emanating from the IPL source when activated; the band pass filter permits transmission of light from the IPL source when activated in the range of about 560 nm to about 690 nm; and, the IPL with the band pass filter provides equivalent cosmetic treatment as a laser with an operating wavelength of 595 nm.

In yet a further aspect, a device for the cosmetic treatment of vascular lesions on skin tissue, wherein the device is an equivalent of a laser having an operating wavelength of 755 nm includes an intense pulsed light (IPL) source, the IPL source being activatable; a band pass filter which blocks substantially all but one range of wavelengths of light emanating from the IPL source when activated; the band pass filter permits transmission of light from the IPL source when activated in the range of about 700 nm to about 800 nm; and, the IPL with the band pass filter provides equivalent cosmetic treatment as a laser with an operating wavelength of 755 nm.

In an aspect, a cosmetic method and apparatus is disclosed for selecting an IPL light source having a band pass filter equivalent to a specified wavelength laser light source for providing cosmetic treatment of skin tissue.

In another aspect, a method of selecting an IPL light source having a band pass filter equivalent to a specified wavelength laser light source for providing cosmetic treatment of skin tissue, the steps includes: selecting an IPL light source having a lamp having a high degree of brightness and being configured to deliver high energy fluences and achieve a threshold energy sufficient to produce a clinical effect during operation; selecting a laser light source of a specified wavelength; activating the laser light source; directing the laser light source at a target; measuring one of: the average absorption coefficient of the selected laser in the target or the average depth of penetration of the selected laser in the target; storing one of: the measured coefficient or the measured depth of penetration; selecting a band pass filter; activating the IPL light source; measuring one of: the average absorption coefficient of the selected band pass filter in the target or the average depth of penetration of the selected band pass filter in the target; comparing the measured coefficient or the depth of penetration of the band pass filter with the stored measured coefficient or the stored measured depth of penetration of the selected laser light source; and, if the measured coefficients or the measured average depths of penetration substantially match, determining that the selected laser light source and the IPL light source with the selected band pass filter are equivalent. The method further includes activating the IPL source and directing it to the skin tissue, wherein the IPL light source filtered with the band pass filter provides equivalent treatment to that of the specified wavelength laser light source.

In yet another aspect, a band pass filter in the range of about 525 nm to about 585 nm provides an equivalent cosmetic treatment effect as a laser with an operating wavelength of 532 nm. Further, a band pass filter in the range of about 560 nm to about 790 nm provides an equivalent cosmetic treatment effect as a laser with a wavelength of 595 nm. Still further, a band pass filter in the range of about 700 nm to about 800 nm provides an equivalent cosmetic effect as a laser with a wavelength of 755 nm.

In an aspect, the method further includes selecting a band pass filter configured to pass light wavelengths in which the ratio of the absorption of light in melanin over the absorption of light in blood is at least above 10.

In another aspect, an IPL system for the cosmetic treatment of vascular lesions on skin tissue, comprises an IPL source/lamp wherein the system uses the activatable intense pulse light (IPL) to mimic the treatment effects of a specific laser used for cosmetic skin treatment, the laser to be mimicked having an operating wavelength of either 532 nm, 595 nm or 755 nm; the system further includes: band pass filters; each of the filters blocking substantially all but one range of wavelengths of light emanating from the IPL source when activated and when interchangeably interposed in the light beam during operation; wherein the band pass filters permit transmission of light from the IPL source when activated in the range of about 525 nm to about 585 nm, for providing an equivalent cosmetic treatment effect as a laser with an operating wavelength of 532 nm, about 560 nm to about 690 nm for providing an equivalent cosmetic treatment effect as a laser with an operating wavelength of 595 nm, about 700 nm to about 800 nm for providing an equivalent cosmetic treatment effect as a laser with an operating wavelength of 755 nm, and wherein the IPL with the band pass filter provides a treatment beam having an absorption coefficient or penetration depth equivalent to that of a selected laser light source, the lamp having a high degree of brightness and being configured to deliver high energy fluences and achieve a threshold energy sufficient to produce a clinical effect during operation.

In yet a further aspect, the IPL source further comprises a handpiece portion which includes the IPL source and an opening in the handpiece portion to accept one or more band pass filters and wherein the one or more band pass filters are filters which pass different ranges of light from the IPL source to the skin tissue.

In an aspect, a method for adapting an IPL system to produce a light beam which is designed to be used during a cosmetic treatment and if used provoking an equivalent treatment effect as a laser with an operating wavelength of 755 nm, 595 nm or 532 nm, the method further comprises: providing an intense pulsed light (IPL) source/lamp having a high degree of brightness being configured to deliver high energy fluences; interposing a band pass filter into the light beam which is configured to deliver a light spectrum which on a weighted average basis has an absorption coefficient value in human skin or anywhere inside the skin which is similar to the absorption coefficient value of a selected laser in a target tissue or chromophore.

In another aspect, a band pass filter is configured to pass light wavelengths in which the ratio of the absorption of light in melanin over the absorption of light in blood is at least above 10.

BRIEF DESCRIPTION OF THE DRAWINGS

FIG. 2 illustrates by a table the absorbent coefficients shown in FIG. 1

FIGS. 8 and 9 illustrate in tabular form typical numerical values of optical absorption at different wavelengths for different chromophores.

DETAILED DESCRIPTION OF THE PRESENT INVENTION

Figure 1:
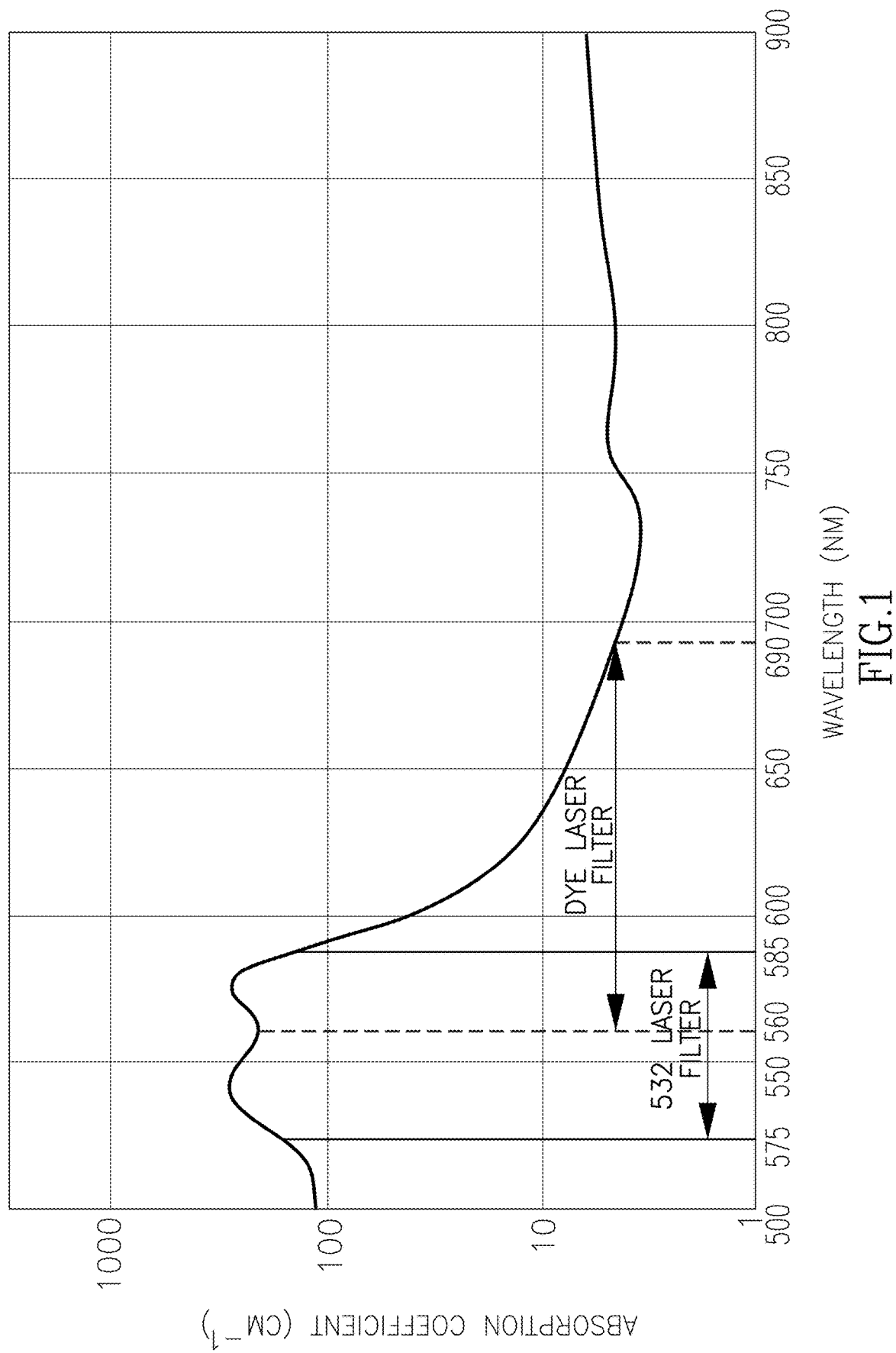
FIG. 1 graphically illustrates absorption of blood by light of various wavelengths.

The absorption coefficient of light in tissue or chromophore is a function of wavelength. Referring now to FIG. 1, shown is a graph of light absorption values in whole blood as a function of wavelength for a "532 laser filter" in "solid lines" and a "Dye laser filter" in "dashed lines". In this non-limiting example, the blood is assumed to consist of about 70% oxyhemoglobin and 30% deoxyhemoglobin on the average. It can be seen that the absorption level varies with the wavelength.

Figure 3:
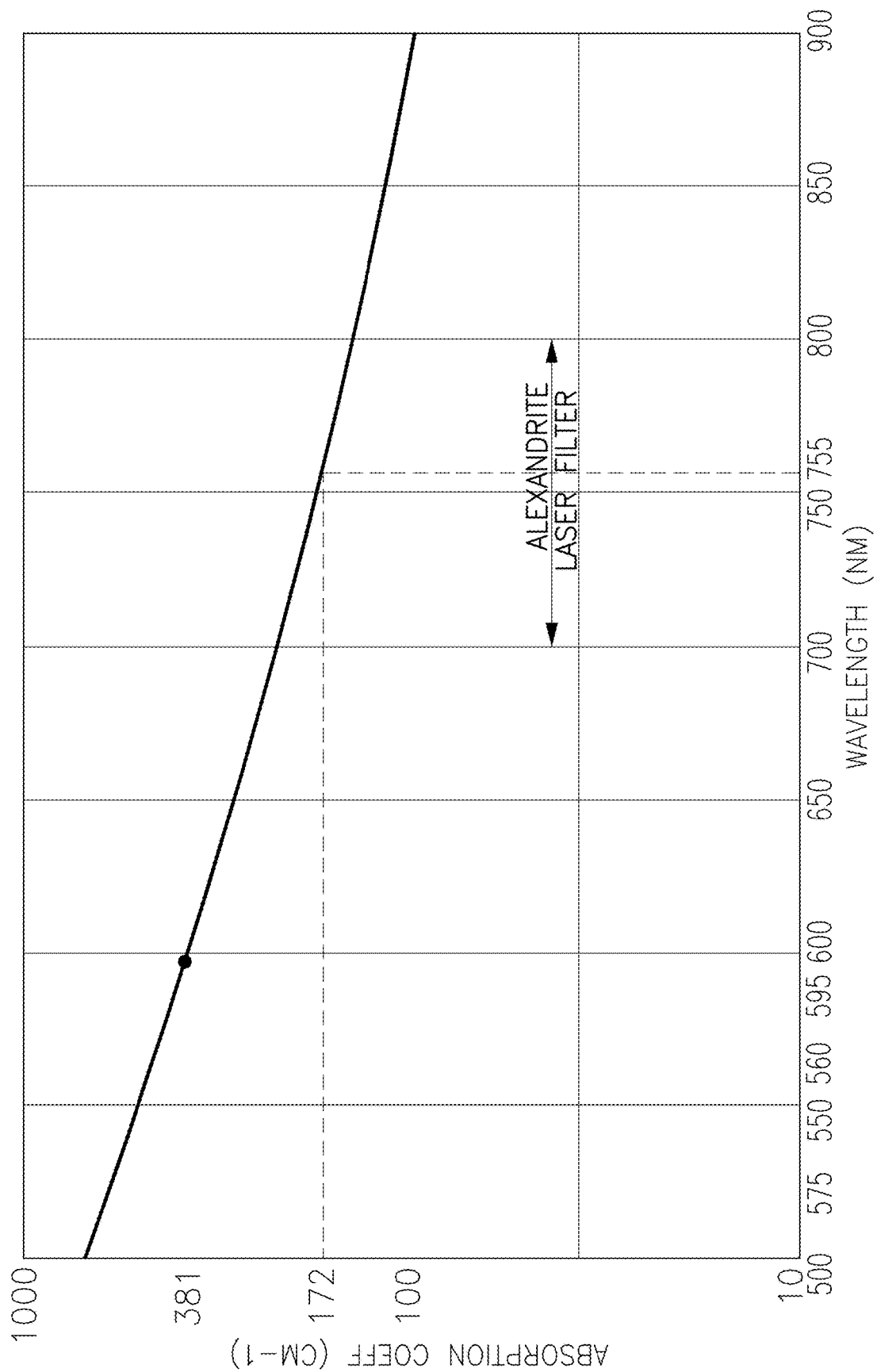
FIG. 3 graphically illustrates absorption of melanin by light in various wavelengths.
Figures 4, 5:
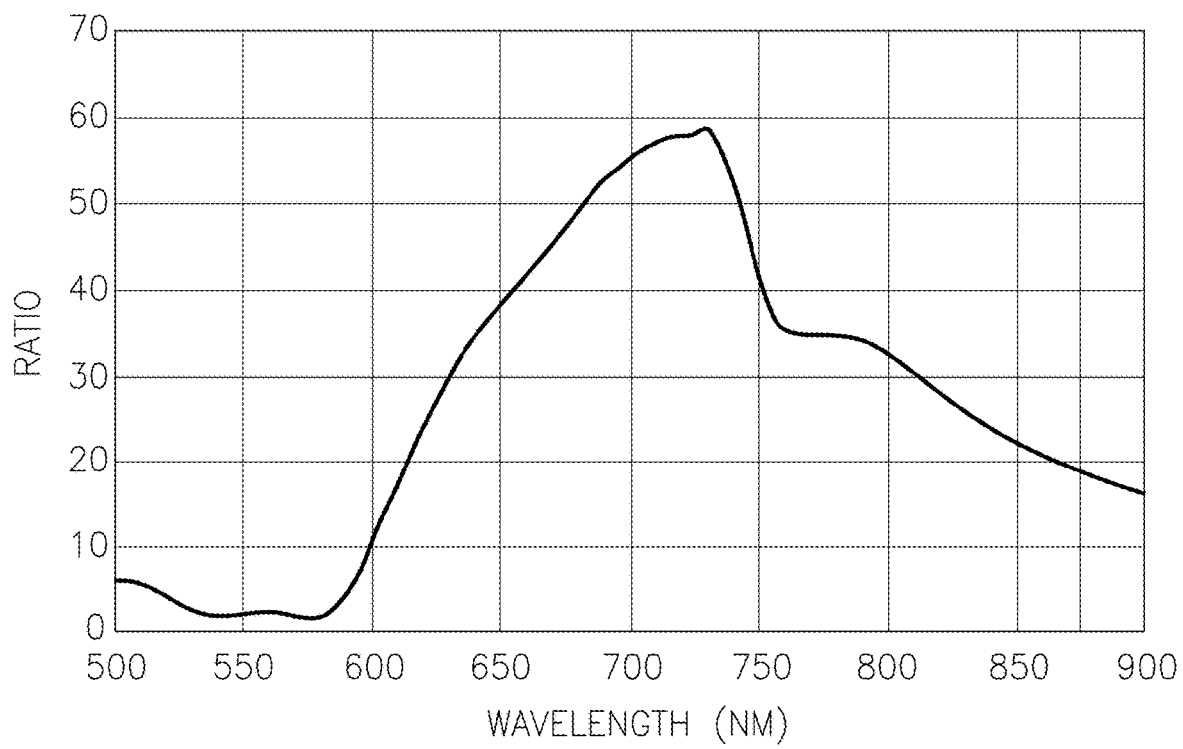
FIG. 4 illustrates in a table the absorbent coefficients shown in FIG. 3.
FIG. 5 illustrates graphically the ratio of the absorption coefficient of light in melanin over blood as a function of wavelength.

FIG. 2 shows a table containing selected numerical values derived from the graph of FIG. 1. Alternatively, FIG. 3 shows a graph of the absorption values of light in melanin as a function of wavelength while FIG. 4 provides selected numerical values derived from the graph of FIG. 3. FIGS. 8 and 9 list typical numerical values of optical absorption at different wavelengths for different chromophores. Average absorption calculations which will be given as examples below are based on these numerical values.

As can be seen, for example, from FIG. 2, the absorption coefficient of blood at a wavelength of 532 nm is about 232 l/cm. Therefore, according to this aspect of the invention, a band pass filter for an IPL system may be provided in the range of 525 to 585 nm, as indicated in FIG. 1 as "532 laser filter" for vascular lesion treatment and as indicated in FIG. 9 which shows an example of a range of wavelengths which can be chosen to provide an equivalent averaged absorption coefficient as provided by the laser. The average absorption coefficient referring to all wavelengths in this range in blood, is equal to the 232 l/cm which characterizes the 532 KTP laser absorbance in blood. Therefore, an IPL system having such a band pass filter would be expected to have a similar tissue interaction on skin as would the 532 nm laser and may be as effective in the treatment of vascular lesions as a 532 nm laser.

As another example illustrated in FIG. 2, a dye laser which has a wavelength of about 595 nm has an absorption coefficient in the blood of about 60 l/cm. The average absorption coefficient value of the band pass filter between 560 nm and 690 nm will have the same average absorption coefficient in blood as a dye laser and therefore, according to this aspect of the invention, an IPL system with a band pass filter of 560 nm to 690 nm, "dye laser filter" as may be seen marked in FIG. 2 as such, may be provided for the treatment of vascular lesions.

As another example, and referring now to FIG. 3, an alexandrine laser (755 nm) has an absorption coefficient of about 172 l/cm in melanin, as may be seen in FIG. 3. A band pass filter from, for example, 700 nm to 800 nm passes a light spectrum which has, on the average, an absorption coefficient in melanin of 173 l/cm and therefore, according to this aspect of the present invention, an IPL system having a band pass filter between 700 nm to 800 nm is provided as an equivalent to an Alexandrite laser and called herein an "Alexandrite laser filter". A band pass filter which passes a light spectrum from 675 nm to 900 nm may provide similar results.

FIG. 8 is a table with examples of ranges of wavelengths which can be chosen to provide, in an IPL device, an equivalent averaged absorption coefficient as the laser Alexandrite. Such an IPL system may be deemed to be characterized with the same or very similar clinical effects as an Alexandrite laser for the treatment of pigmented lesions.

According to another aspect of the present invention, an IPL system may be provided having an IPL handpiece which has a permanent embedded filter which is configured to hold a band pass filter which delivers a spectrum of light which has an average absorption coefficient which is about similar to the absorption coefficient of one of the known laser wavelengths, such as for example KTP, 532 nm, pulsed dye laser (PDL) 585 nm-595 nm, Alexandrite 755 nm, diode laser 800-810 nm and Nd:YAG 532, Ruby 694 nm or 1,064 nm and more.

According to yet another aspect of the present invention, an IPL system with an IPL handpiece may be configured to accept different filters, each in accordance with the present invention, so that a single handpiece may interchangeably deliver light spectrums which have average absorption coefficients on a target tissue or chromophore similar to those of equivalent known lasers. A device manufactured and sold by the assignee of the present invention, Lumenis LTD of Israel, named the M22 Universal IPL, is an example of such a device that accepts different filters.

Figure 6:
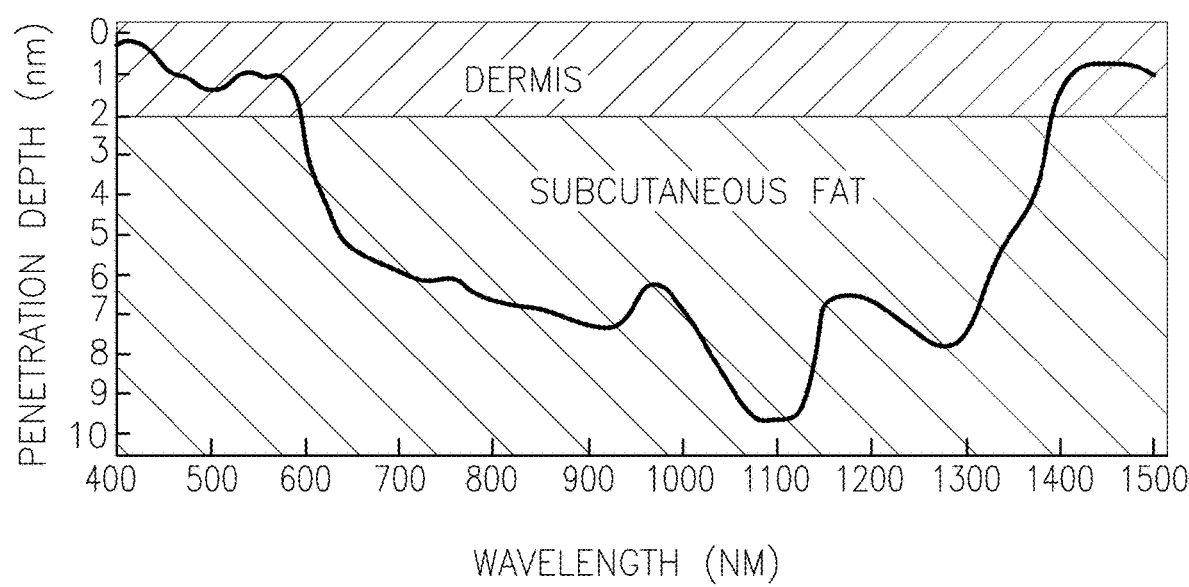
FIG. 6 illustrates graphically penetration depths of light into tissue at various wavelengths.

The average calculation of a series of absorption values associated with a certain light spectrum which is passed through a band pass filter as described above, can be made in different ways. In the above examples, the calculation of the average was a basic arithmetic average calculation in which the "weight" of each wavelength is similar. However, as can be seen in FIG. 6, the penetration depth of light into a tissue, such as skin, varies and is also a function of wavelength. Therefore, according to another aspect of the invention, the average absorption coefficient of a spectrum of light passed through a band pass filter in accordance with the present invention may be calculated based on a weighted average calculation.

Moreover, due to the dependency of the depth of penetration on the wavelength, spots in different depths in the skin will experience different effective wavelength intensity distribution. In general, there is a shift towards red and mid-infrared of the spectrum as depth increases. Therefore, according to this aspect of the present invention, an IPL system is provided having an IPL band pass filter which is configured to deliver a spectrum of light which has an average absorption coefficient of a target tissue or chromophore which is similar to the absorption coefficient of a known laser at a predefined depth in the skin.

For example, on the skin surface, an Alexandrite laser of 755 nm has an absorption value of an about 172 l/cm in melanin, as can be seen in FIG. 4. As can be seen in FIG. 3, a spectrum of light which on the average will have a similar absorption in melanin as the Alexandrite laser may be a band pass filter of 700 nm to 800 nm. It should be mentioned that different band pass filters may also, on the average, produce a spectrum with an averaged absorption coefficient similar to an Alexandrite laser, for example, a band pass filter of 725 nm to 775 nm.

As mentioned above, a critical energy threshold also preferably is reached in order to achieve a required clinical effect. Therefore, a band pass filter should be chosen, based on the lamp performances and intensity, to not only deliver a spectrum having an average light absorption in a target tissue or chromophore similar to that of a known laser but also to deliver at least the threshold energy to achieve a clinical effect. Turning attention now back to the example concerning the depth of a target tissue in the skin, an Alexandrite laser filter for pigmented lesion, which aims to target melanin deeper in the skin due to the shift toward mid-infrared, may need to deliver a slightly different light spectrum shifted toward blue, in order to keep the average absorption value of the delivered spectrum around the 172 l/cm+ at this deeper location.

Figure 7:
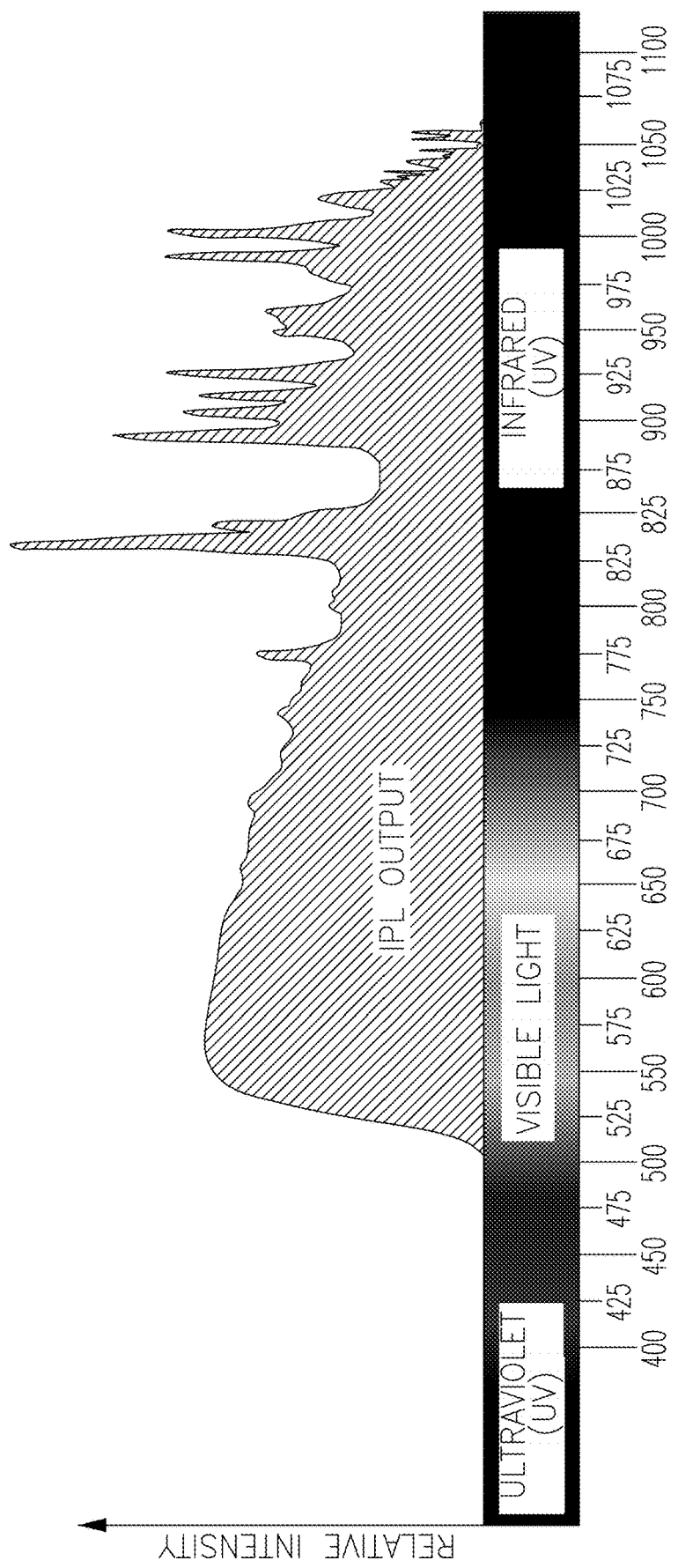
FIG. 7 illustrates graphically at different wavelengths the relative efficiency of IPL light sources.

According to another aspect of the present invention, as can be seen in FIG. 7, the energy emitted from a lamp is also a function of wavelength. At different wavelengths, the efficiency of the lamp is different and therefore a different amount of energy is irradiated and delivered Therefore, as mentioned above, a weighted average calculation may be performed in order to compensate for uneven energy distribution of the lamp. An IPL system and an appropriate band pass filter which is configured to deliver a light spectrum which on a weighted average basis has an absorption coefficient value in the skin or anywhere inside the skin which is similar to the absorption coefficient value of a known laser in a target tissue or chromophore is also an aspect of the present invention.

FIG. 5 shows the ratio of the absorption coefficient of light in melanin over blood as a function of the wavelength. As can be seen, in a wavelength range of 600 nm to 900 nm, the ratio is higher than 10. Therefore, according to this aspect of the present invention, the band pass filter of the present invention may be configured to pass a spectrum of wavelengths in which the ratio of the absorption of light in melanin over the absorption of light in blood is at least above 10 l/cm. A ratio higher than 10 l/cm will be expected to produce good selectivity for the treatment of pigmented lesion. According to another embodiment, an IPL system may be configured to deliver a light spectrum having a ratio larger than 20 l/cm, larger than 30 l/cm, larger than 40 l/cm or larger than 50 l/cm to further enhance selectivity. According to this aspect of the invention, and to other aspects of the present invention, a lamp having a high degree of brightness is configured to deliver high energy fluences and therefore, even with the use of a relatively narrow band pass filters, a threshold energy sufficient to produce a clinical effect will be achieved.

One example of a suitable flash lamp for practicing the present invention may be that flashlamp structure as described in U.S. Provisional Application Ser. No. 62/465,210, filed Mar. 1, 2017.

What is claimed is:

1. A method of selecting an IPL light source having a band pass filter equivalent to a specified wavelength laser light source for providing cosmetic treatment of skin tissue, the steps comprising:
    selecting an IPL light source having a lamp having a high degree of brightness and being configured to deliver high energy fluences and achieve a threshold energy sufficient to produce a clinical effect during operation;
    selecting a laser light source of a specified wavelength;
    activating the laser light source;
    directing the laser light source at a target;
    measuring one of: the average absorption coefficient of the selected laser in the target or the average depth of penetration of the selected laser in the target;
    storing one of: the measured coefficient or the measured depth of penetration;
    selecting a band pass filter;
    activating the IPL light source;
    measuring one of: the average absorption coefficient of the selected band pass filter in the target or the average depth of penetration of the selected band pass filter in the target;
    comparing the measured coefficient or the depth of penetration of the band pass filter with the stored measured coefficient or the stored measured depth of penetration of the selected laser light source; and,
    if the measured coefficients or the measured average depths of penetration substantially match, determining that the selected laser light source and the IPL light source with the selected band pass filter are equivalent.

2. The method of claim 1, further comprising activating the IPL source and directing it to the skin tissue, wherein the IPL light source filtered with the band pass filter provides equivalent treatment to that of the specified wavelength laser light source.

3. The method of claim 2, wherein a band pass filter in the range of about 525 nm to about 585 nm provides an equivalent cosmetic treatment effect as a laser with an operating wavelength of 532 nm.

4. The method of claim 2, wherein a band pass filter in the range of about 560 nm to about 790 nm provides an equivalent cosmetic treatment effect as a laser with a wavelength of 595 nm.

5. The method of claim 2, wherein a band pass filter in the range of about 700 nm to about 800 nm provides an equivalent cosmetic effect as a laser with a wavelength of 755 nm.

6. A method according to claim 5 for adapting an IPL system to produce a light beam which is designed to be used during a cosmetic treatment and if used provoking an equivalent treatment effect as a laser with an operating wavelength of 755 nm, 595 nm or 532 nm, the method further comprising:
    providing an intense pulsed light (IPL) source/lamp having a high degree of brightness being configured to deliver high energy fluences; interposing a band pass filter into the light beam which is configured to deliver a light spectrum which on a weighted average basis has an absorption coefficient value in human skin or anywhere inside the skin which is similar to the absorption coefficient value of a selected laser in a target tissue or chromophore.

7. The method of claim 2, further comprising selecting a band pass filter configured to pass light wavelengths in which the ratio of the absorption of light in melanin over the absorption of light in blood is at least above 10.

* * * * *